United States Patent [19]
Yamamoto et al.

[11] Patent Number: 4,734,281
[45] Date of Patent: Mar. 29, 1988

[54] METHOD FOR CONCURRENTLY EMITTING VAPORS OF SEX PHEROMONES OF DIFFERENT INSECTS

[75] Inventors: Akira Yamamoto, Niigata; Kinya Ogawa, Kanagawa; Shigehiro Nagura, Niigata, all of Japan

[73] Assignee: Shin-Etsu Chemical Co., Ltd., Tokyo, Japan

[21] Appl. No.: 9,458

[22] Filed: Feb. 2, 1987

[30] Foreign Application Priority Data

Feb. 5, 1986 [JP] Japan .................................. 61-23602

[51] Int. Cl.$^4$ ............................................. A01N 25/34
[52] U.S. Cl. .................... 424/408; 424/405; 424/452; 424/84; 514/513
[58] Field of Search ................ 424/452, 408, 409, 84; 514/842, 957, 513, 693

[56] References Cited

U.S. PATENT DOCUMENTS 3,539,465 11/1970 Hiestand et al. .................... 252/316
3,577,515 5/1971 Vandegaer ............................ 424/32
4,600,146 7/1986 Ohno ....................................... 239/6

FOREIGN PATENT DOCUMENTS 57-139005 8/1982 Japan .................................. 424/331
57-146703 9/1982 Japan .................................. 514/842
57-150603 9/1982 Japan .................................. 514/842

Primary Examiner—Thurman K. Page
Attorney, Agent, or Firm—Hopgood, Calimafde, Kalil, Blaustein & Judlowe

[57] ABSTRACT

An efficient cost- and labor-saving method is proposed for controlling the population of two kinds or more of different species of insectan pests in a field by means of distributing dispensers of sex pheromone compounds for the respective species of the insects when one of the sex pheromone compounds is an unsaturated $C_{10}$ to $C_{12}$ alcohol and the other is an unsaturated $C_{14}$ to $C_{20}$ acetate or aldehyde. When these two classes of the compounds are mixed in such a proportion that the overall solubility paramater $\delta$ of the mixture is 9.1 to 9.7 and the mixture is contained in a dispenser body made of polyethylene or a copolymer mainly composed of ethylene moiety, the two compounds can be concurrently emitted from the dispenser in the form of vapor each at a controlled rate over a desired length of time.

3 Claims, No Drawings

METHOD FOR CONCURRENTLY EMITTING VAPORS OF SEX PHEROMONES OF DIFFERENT INSECTS

BACKGROUND OF THE INVENTION

The present invention relates to a method for concurrently emitting sex pheromones of insects in the form of vapor to the atmospheric air at controlled rates or, more particularly, to a method for emitting vapors of two or more kinds of sex pheromone compounds each having activity to different species of noxious insects to the atmosphere concurrently at controlled rates.

It is widely practiced in recent years that a synthetically prepared specific chemical compound called a sex pheromone having activity to a specific species of insects is utilized in the industries of agriculture and forestry for the purpose of controlling the population of insectan pests in the fields such as farms, orchards and forests. A sex pheromone of insects is a compound having attracting activity to one of the sexes of the insectan individuals of a particular species so as to disrupt the intersexual communication and the copulation behavior of the sexes resulting in decreased rate of multiplication. It is noteworthy that the effective concentration of a sex pheromone of insects is usually extremely low in the atmospheric air.

When a sex pheromone compound is used in the field for controlling the population of a particular species of insectan pests, it is a usual practice that, instead of distributing the pheromone compound as such over the field, the pheromone compound is contained in a shaped body and the body containing or impregnated with the pheromone compound is used as a dispenser by distributing a large number of such dispensers over the field so that vapor of the pheromone compound is sustainedly released therefrom at a controlled rate over a period of time.

For example, German Patent Nos. 28 32 248 and 29 45 655 teach a dispenser of a sex pheromone compound which is a bag made of a plastic film and containing the sex pheromone compound so that the compound permeates the bag walls and the vapor thereof is released to the atmosphere. U.S. Pat. No. 4,600,146 teaches a plastic-made tubular dispenser body containing the sex pheromone compound in the capillary bore thereof so that the sex pheromone compound permeates the tube walls and is released to the atmosphere in the form of vapor off the outer surface. The tubular dispenser should preferably be bonded side-by-side in the longitudinal direction with a metal wire having plastic deformability so that the dispenser body can retain any form as bent to ensure convenience and reliability in fixedly installing the dispensers having an appropriately deformed configuration in desired positions, e.g. on the twigs in an orchard.

It is a generally undertaken practice in the prior art that a single vapor dispenser contains only a single sex pheromone compound or, if not, a mixture of a pheromone compound with one or more related compounds such as geometrical isomers of the particular pheromone compound so that it is a relatively easy matter to control the rate of vapor release from a numer of vapor dispensers.

When two species or more of insectan pests should be controlled in respective populations by using sex pheromone compounds each having activity only to one of the species, however, vapors of different pheromone compounds must be emitted to the field concurrently each at a controlled rate so that the dispensers distributed over the field should be divided into groups in such a manner that dispensers of a group contain the sex pheromone compound effective to the first species while the dispensers of the other group contain a different sex pheromone compound effective to the second species. Accordingly, the dispensers of these gorups must be prepared and distributed over the field group by group so that the overall costs for the pest control are unavoidably multiplied as a matter of course.

When a first sex pheromone compound is an aliphatically unsaturated alcohol having 10 to 12 carbon atoms while a second sex pheromone compound, the vapor of which should desirably be emitted concurrently with the first, is an aliphatically unsaturated ester or aldehyde having 14 to 20 carbon atoms, in particular, no method is known in the prior art to be deemed impossible for simultaneously controlling the rates of concurrent emission of these two types of pheromone compounds by using vapor dispensers of a single type due to the so widely different physical parameters between the compounds such as the boiling point which is much lower in the former compound than in the latter compound and the vapor pressure at room temperature which is much higher in the former compound than in the latter compound.

Various types of vapor dispensers are known in the prior art including those prepared by impregnating a porous carrier material with a sex pheromone compound and those of the spirit-lamp type in which the surface area available for the vaporization of the pheromone compound is kept constant. The mixed vapor of the different kinds of the pheromone compounds is emitted to the atmosphere without a barrier from these dispensers. Dispensers of such a barrier-free type are also not satisfactory in respect of the simultaneous control of the emission rates of the different sex pheromone compounds because liquid compounds in a mixture generally cannot be vaporized at rates proportional to their respective fractions in the mixture and the compound having a higher vapor pressure is preferentially vaporized leaving the mixture leaned of the component.

The solubility parameter denoted by a symbol $\delta$ is one of the physical parameters greatly differing between the above mentioned two types of the insectan sex pheromone compounds. The value of $\delta$ can be obtained by the method developed by Robert F. Fedors and described in Polymer Engineering and Science, volume 14 (1974), page 147 by the calculation using an equation $$\delta = (\Sigma \Delta e_i / \Sigma \Delta v_i)^{\frac{1}{2}},$$

in which $\Delta e_i$, given in calories/mole, is the contribution of a particular atom or atomic group to the energy of vaporization and $\Delta v_i$, given in cm$^3$/mole, is the contribution of the particular atom or atomic group to the molar volume.

Application of the above described method to the determination of the solubility parameters $\delta$ of the above mentioned two types of the sex pheromone compounds gives a value of $\delta = 9.9$ to $10.1$ for the unsaturated alcohols and a value of $\delta = 8.6$ to $9.0$ for the unsaturated acetates and aldehydes. When these two types of the compounds having so widely different values of the solubility parameter $\delta$ are contained in a single dispenser having plastic-made walls in the form of, for example, tubes, bags, capsules and laminates, the rates of vapor release of the respective pheromone compounds through the plastic-made walls are greatly influenced by the value of the solubility parameter $\delta$. When the dispenser walls are formed of a plastic resin having low polarity, such as polyethylenes, for example, the unsaturated acetate or aldehyde compound having 14 to 20 carbon atoms in a molecule can permeate the dispenser walls and is released to the atmosphere in the form of vapor at a controlled rate while unsturated alcohols having 10 to 12 carbon atoms in a molecule can hardly permeate the dispenser walls due to the poor affinity thereof with the polyethylene-made walls so that polyethylene-made dispensers cannot be used in the object of sustainedly releasing vapor of such an unsaturated alcohol compound as a sex pheromone of insects.

When the dispenser is formed of a plastic resin having relatively large polarity, such as an ethylene-vinyl alcohol copolymer, on the other hand, unsaturated alcohols having 10 to 12 carbon atoms in a molecule can permeate the dispenser walls at a controlled rate while dispensers made of such a plastic resin cannot be used for the purpose of sustained vapor release of the unsaturated acetates and aldehydes having 14 to 20 carbon atoms in a molecule at a controlled.

Thus, it is a generally accepted conclusion in the prior art that it would be a very difficult matter to simultaneously controlling the rates of vapor release of two different sex pheromone compounds having widely different values of solubility parameter $\delta$ by using a single type of a dispenser form.

SUMMARY OF THE INVENTION

Thus, the present invention has an object to provide a novel means for simultaneously controlling the rates of concurrently released vapors of two different kinds of sex pheromone compounds having different values of solubility parameter $\delta$ by using a dispenser form containing both of the compounds.

More particularly, the object of the present invention is to provide a means for simultaneously controlling the rates of concurrent vapor release of two insectan sex pheromone compounds including an aliphatically unsaturated alcohol having 10 to 12 carbon atoms in a molecule and an aliphatically unsaturated acetate or aldehyde having 14 to 20 carbon atoms in a molecule.

Thus, the method of the present invention for simultaneously controlling the rates of concurrent vapor release of a first sex pheromone compound of insects which is an aliphatically unsaturated alcohol having 10 to 12 carbon atoms in a molecule and a second sex pheromone compound of insects which is an aliphatically unsaturated acetate or aldehyde having 14 to 20 carbon atoms in a molecule comprises:

(a) mixing the first and the second pheromone compounds into a liquid mixture; and (b) enclosing the liquid mixture in a container having a wall made of a polyethylene or a copolymer of ethylene comprising at least 90% by weight of an ethylene moiety so that the first and the second sex pheromone compounds concurrently permeate the wall as a barrier and are released to the atmosphere in the form of vapor.

DETAILED DESCRIPTION OF THE PREFERRED EMBODIMENTS

As is understood from the above given summary of the invention, the characterstic feature of the inventive method consists in the mixing of the two sex pheromone compoundsinto a liquid mixture which should be contained in a dispenser body having a wall made of a polyethylene or a copolymer of ethylene.

The first of the sex pheromone compounds of insects should be an aliphatically unsaturated alcohol having 10 to 12 carbon atoms in a molecule usually having a solubility parameter $\delta$ in the range from 9.9 to 10.1. Two kinds or more of such alcoholic compounds may be used in combination, if necessary. The second of the sex pheromone compounds should be an aliphatically unsaturated acetate or aldehyde compound having 14 to 20 carbon atoms in a molecule generally having a solubility parameter $\delta$ in the range from 8.6 to 9.0. Two kinds or more of such acetate and/or aldehyde compounds can be used in combination, if necessary. In mixing these two types of the sex pheromone compounds into a liquid mixture, the mixing ratio should preferably be such that the resultant mixture has a value of the solubility parameter in the range from 9.1 to 9.7. It is noteworthy that, while the above mentioned unsaturated alcohol compound can hardly permeate a polyethylene film when it is alone, the unsaturated alcohol compound can permeate a polyethylene film when it is in a mixture with one or more of the above mentioned unsaturated acetate and/or aldehyde compounds at a relatively constant rate over a long period of time and is released to the atmosphere in the form of vapor. This is a quite unexpected discovery and the effect is equally obtained for a mixture of the sex pheromone compounds having an overall solubility parameter $\delta$ of 9.1 to 9.7 when the plastic resin forming the dispenser wall is, in place of a homopolymeric polyethylene, a copolymer of ethylene composed of at least 90% by weight of the moiety of ethylene. Such a copolymer is exemplified by copolymers of ethylene and vinyl acetate in a copolymerization ratio of 90:10 to 97:3 by weight. When a polyethylene or a copolymer of ethylene is used as a material of the vapor dispenser, not only the rates of the concurrent vapor release of the two kinds of the sex pheromone compounds can be controlled simultaneously but also the loss of the pheromone compounds by adsorption is greatly decreased.

The vapor dispenser used in the inventive method having a wall of a polyethylene or a copolymer of ethylene can be in the form of tubes, bags, capsules, laminates and the like without particular limitations.

Exemplary of the aliphatically unsaturated alcohol having 10 to 12 carbon atoms in a molecule and a solubility parameter $\delta$ of 9.9 to 10.1 and effective as a sex pheromone of an insectan pest are E,E-8,10-dodecadienol having a value of $\delta$ of 9.9 and E-5-decenol having a value of $\delta$ of 10.1 as well as isomers thereof. Exemplary of the aliphatically unsaturated acetate and aldehyde having 14 to 20 carbon atoms in a molecule and a solubility parameter $\delta$ of 8.6 to 9.0 and effective as a sex pheromone of an insectan pest are Z-8-dodecenyl acetate having a $\delta$ of 8.7, 11-tetradecenyl acetate having a value of $\delta$ of 8.6, Z,Z-3,13-octadecenyl acetate having a value of $\delta$ of 8.6 and Z,Z-10,13-hexadecadienal having a value of $\delta$ of 9.0 as well as isomers thereof.

The overall solubility parameter $\delta$ of a mixture of two sex pheromone compounds can be calculated from the weight fractions of the respective compounds in the mixture and the solubility parameter δ of each component since the rule of additivity is held between the components and the mixture. When the overall value of the solubility parameter δ of the pheromone mixture is outside the above mentioned range of 9.1 to 9.7, the rates of the sustained vapor release of the compounds cannot be controlled satisfactorily.

In contrast to the general practice in the prior art that, when two different species of insectan pests should be simultaneously controlled relative to their populations in the same field by disrupting the intersexual communication using an unsaturated alcohol compound having 10 to 12 carbon atoms in a molecule against one species and an unsaturated acetate or aldehyde compound having 14 to 20 carbon atoms in a molecule against the other species, the respective pheromone compounds must be separately prepared in the form of dispensers and two groups of dispensers must be separately distributed over the field each group in a specified density, the present invention provides a possibility of great saving of the costs including the cost for the preparation of dispensers and the cost for the distribution of the dispensers over the field since the two different pheromone compounds can be prepared in the form of dispensers as a mixture and the vapors of the two pheromones can be emitted to the field each at a controlled rate by distributing a single set of the dispensers containing the mixture.

For example, American and European orchards suffer sometimes simultaneously from various species of insectan pests including one species or more of codling moths and peach twig borers to which the applicable sex pheromones are E,E-8,10-dodecadienol and E-5-decenol, respectively, each belonging to the class of the unsaturated alcohols having 10 to 12 carbon atoms in a molecule and one species or more of oriental fruit moths, leaf rollers, navel orange worms and peach tree borers to which the applicable sex pheromones are Z-8-dodecenyl acetate, 11-tetradecenyl acetate, Z,Z-11,13-hexadienal and 3,13-octadecadienyl acetate, respectively, each belonging to the class of the unsaturated acetates and aldehydes having 14 to 20 carbon atoms in a molecule. The present invention provides a very economical method for simultaneously controlling these two classes of the insectan pests by distributing a single form of pheromone dispensers over the field for disrupting the intersexual communication in contrast to the prior art method in which at least two groups of the pheromone dispensers should be prepared and distributed.

EXAMPLE 1

A number of polyethylene tubes each having an inner diameter of 0.8 mm, outer diameter of 1.4 mm and length of 200 mm were filled each with 80 mg of a 50:50 by weight mixture of E,E-8,10-dodecadienol, i.e. the sex pheromone of codling moths, and Z-8-dodecenyl acetate, i.e. the sex pheromone of oriental fruit moths, having an overall solubility parameter δ of 9.3 and the ends of the tubes were sealed to give dispensers of combined sex pheromones.

The pheromone dispensers were kept at 30° C. in an air stream of a velocity of 0.5 meter/second to determine the rate of vapor release of each of the two pheromone compounds by the gas chromatographic analysis of the collected portion using an internal standard. The results were that the rates were 0.4 mg/day and 0.5 mg/day for E,E-8,10-dodecadienol and for Z-8-dodecenyl acetate, respectively, and were approximately constant over a period of 60 days.

COMPARATIVE EXAMPLE

The same polyethylene tubes as used in Example 1 were filled each with 80 mg of a 90:10 by weight mixture of E,E-8,10-dodecadienol and Z-8-dodecenyl acetate having an overall solubility parameter δ of 9.8 and the ends of the tubes were sealed to give dispensers of combined pheromones. The vapor release test of the thus prepared pheromone dispensers indicated that E,E-8,10-dodecadienol was emitted for the first 10 days at a rate of 0.2 mg/day or smaller but the rate of vapor release of this compound was negligibly smaller thereafter.

EXAMPLE 2

The same polyethylene tubes as used in Example 1 were filled each with 80 mg of a 40:60 by weight mixture of E-5-decenol, i.e. the sex pheromone of peach twig borers, and Z-11,13-hexadecadienal, i.e. the sex pheromone of navel orange worms having an overall solubility parameter δ of 9.4 and sealed at both ends. The thus prepared pheromone dispensers were subjected to the test of the vapor release rates in the same manner as in Example 1 to give the results that the rates were 0.4 mg/day and 0.4 mg/day for E-5-decenol and for Z-11,13-hexadecadienal, respectively, and were approximately constant over a period of 60 days.

EXAMPLE 3

The same polyethylene tubes as used in Example 1 were each filled in the same manner as in Example 1 with 80 mg of a mixture composed of each 20% by weight of E,E-8,10-dodecadienol, E-5-decenol, Z-8-dodecenyl acetate, 11-tetradecenyl acetate, i.e. the sex pheromone of leaf rollers, and Z,Z-3,13-octadecadienyl acetate, i.e. the sex pheromone of peach tree borers, having an overall solubility parameter δ of 9.2. The pheromone dispensers were subjected to the test of the rates of vapor release in the same manner as in Example 1 to find that the rates were 0.15 mg/day, 0.15 mg/day, 0.2 mg/day, 0.15 mg/day and 0.05 mg/day for the above mentioned five kinds of the pheromone compounds, respectively, and the rates were approximately constant over a period of 50 days.

EXAMPLE 4

A 20 mg portion of a 50:50 by weight mixture of E,E-8,10-dodecadienol and 11-tetradecenyl acetate having an overall solubility parameter δ of 9.3 was injected into a hollow sphere having an inner diameter of 4 mm and a wall thickness of 0.4 mm made of a copolymer of ethylene and vinyl acetate in a copolymerization ratio of 97:3 by weight using an injector. The thus prepared pheromone dispenser was subjected to the test of the rates of vapor release in the same manner as in Example 1 to find that the rate was 0.1 mg/day for each of the pheromone compounds and the rate ws approximately constant over a period of 70 days.

What is claimed is:

1. A method for simultaneously controlling the rates of concurrent vapor release of a first sex pheromone compound of insects which is an aliphatically unsaturated alcohol having 10 to 12 carbon atoms in a molecule and a second sex pheromone compound of insects which is an aliphatically unsaturated acetate or aldehyde having 14 to 20 carbon atoms in a molecule, which comprises:
  (a) mixing the first and the second sex pheromone compounds of insects into a liquid mixture; and
  (b) enclosing the liquid mixture in a container having a wall made of a polyethylene or a copolymer of ethylene composed of at least 90% by weight of an ethylene moiety so that the first and the second sex pheromone compounds concurrently permeate the wall as a barrier and are released to the atmosphere in the form of vapor.

2. A method for simultaneously controlling the rates of concurrent vapor release of a first sex pheromone compound of insects which is an aliphatically unsaturated alcohol having 10 to 12 carbon atoms in a molecule and a solubility parameter $\delta$ in the range from 9.9 to 10.1 and a second sex pheromone compound of insects which is an aliphatically unsaturated acetate or aldehyde having 14 to 20 carbon atoms in a molecule and a solubility parameter $\delta$ in the range from 8.6 to 9.0, which comprises:
  (a) mixing the first and the second sex pheromone compounds of insects into a liquid mixture in such a proportion that the mixture has an overall solubility parameter $\delta$ in the range from 9.1 to 9.7; and
  (b) enclosing the liquid mixture in a container having a wall made of a polyethylene or a copolymer of ethylene composed of at least 90% by weight of an ethylene moiety so that the first and the second sex pheromone compounds concurrently permeate the wall as a barrier and are released to the atmosphere in the form of vapor.

3. A method for simultaneously controlling the rates of concurrent vapor release of a first sex pheromone compound of insects selected from the group consisting of E,E-8,10-dodecadienol and E-5-decenol and a second sex pheromone compound of insects selected from the group consisting of Z-8-dodecenyl acetate, 11-tetredecenyl acetate, Z,Z-3,13-octadecenyl acetate and Z,Z-11,13-hexadecadienal which comprises:
  (a) mixing the first and the second sex pheromone compounds of insects into a liquid mixture in such a proportion that the mixture has an overall solubility parameter $\delta$ in the range from 9.1 to 9.7; and
  (b) enclosing the liquid mixture in a container having a wall made of a polyethylene or a copolymer of ethylene composed of at least 90% by weight of an ethylene moiety so that the first and the second sex pheromone compounds concurrently permeate the wall as a barrier and are released to the atmosphere in the form of vapor.

* * * * *

UNITED STATES PATENT AND TRADEMARK OFFICE
CERTIFICATE OF CORRECTION

PATENT NO. : 4,734,281

DATED : March 29, 1988

INVENTOR(S) : Akira Yamamoto, et al.

It is certified that error appears in the above-identified patent and that said Letters Patent is hereby corrected as shown below:

In claim 3, lines 13 and 14, kindly delete "11-tetredecenyl"

and insert therefore --11-tetradecenyl--.

Signed and Sealed this

Twenty-third Day of August, 1988

*Attest:*

DONALD J. QUIGG

*Attesting Officer*  *Commissioner of Patents and Trademarks*